United States Patent [19]
Pfab et al.

[11] Patent Number: 5,018,527
[45] Date of Patent: May 28, 1991

[54] SENSOR FOR THE MEASUREMENT OF ION ACTIVITY

[75] Inventors: Werner Pfab, Zirndorf; Michael Bergmann; Paul-Gerhard Fenzlein, both of Nuremberg; Wolfgang Anderer, Aurachtal, all of Fed. Rep. of Germany

[73] Assignee: Siegert GmbH

[21] Appl. No.: 226,066

[22] Filed: Jul. 28, 1988

[30] Foreign Application Priority Data

Aug. 1, 1987 [DE] Fed. Rep. of Germany ....... 3725597
Mar. 25, 1988 [DE] Fed. Rep. of Germany ....... 3810186

[51] Int. Cl.$^5$ ............................................. A61B 5/00
[52] U.S. Cl. .................................. 128/635; 204/403; 204/416
[58] Field of Search ................. 128/635; 204/403, 416

[56] References Cited

U.S. PATENT DOCUMENTS 4,340,457 7/1982 Kater .................................. 128/635
4,600,495 7/1986 Fogt .................................. 128/635 X
4,653,499 3/1987 Murray, Jr. et al. ................ 128/635

FOREIGN PATENT DOCUMENTS 2000294 1/1979 United Kingdom ............... 128/635

OTHER PUBLICATIONS

Kimura et al., "An Integrated ... Biosensor", Sensors & Actuators, 9 (1986), 373-387.
Drug Research, "Theory and Application of Ion-Selective Electrodes in Physiology and Medicine", pp. 17 & 22, Jul. 1977.

*Primary Examiner*—Lee S. Cohen
*Attorney, Agent, or Firm*—Toren, McGeady & Associates

[57] ABSTRACT

A sensor for measuring the activity of ions by means of ion-selective membranes (4) improves the measuring possibilities and reduces the dimensions of the sensor in that a plurality of such membranes are held in a common carrier (3) and are electrically insulated and protected against the penetration of moisture. Shunts (2) are provided in a sensor body (1) of the carrier. The carrier and sensor body are connected to one another. The invention is also directed to a method for producing such a sensor. Moreover, the invention is concerned with sensors and a respective arrangement for hemodialysis.

34 Claims, 10 Drawing Sheets

SENSOR FOR THE MEASUREMENT OF ION ACTIVITY

FIELD AND BACKGROUND OF THE INVENTION

The invention is directed first to a sensor for measuring ionic activity by means of ion-selective membranes and associated shunts or leak conductances. Such an ion-selective membrane comprises a PVC base structure into which ionophori which are selected in accordance with the ions to be measured are introduced in determined quantitative ratios. Ionophori (called in German Ionophore) is used here as the plural of "ionophorus". Such ionophori are chemical compounds of a very particular structure which are known from the prior art. According to the quantity of active (free) ions, a certain phase boundary potential is formed at the membrane and toward the shunt contacting the membrane. This phase boundary potential can be viewed as the electromotive force (EMF) of an electrochemical half cell and is a measurement for the measured ionic activity. Ionometric sensors are known for carrying out serum and whole blood analysis in the area of a patient being tested bedside monitoring and in the laboratory. The blood, whose ionic activities are to be measured, is removed as a specimen (i.e., invasively) and introduced in the ionometer, wherein it is conducted past a series of membranes, (i.e., a flow-type electrode). It is disadvantageous that such an ionometer is suitable only for the very particular application described above, and that a determined quantity of whole blood (at least 2 to 3 ml) must be drawn from the patient for each measurement. This is particularly stressing for anemic (dialysis) patients and children. Moreover, there is an acute risk of infection, in principle, for the personnel every time blood is removed (particularly hepatitis B and AIDS).

SUMMARY OF THE INVENTION

An object of the invention is to construct a sensor for measuring ionic activity by means of ion-selective membranes and respective shunts such that a plurality of membranes and, accordingly, a plurality of simultaneous possibilities for noninvasive measurement of different or identical ions, are available for the entire medical and biological (therapeutic and diagnostic) area or fluids to be tested, and wherein it should be possible to accommodate such a sensor in a very compact space.

To this end, the sensor according to the invention firstly includes at least two ion-selective membranes which are held in a common insulating carrier for simultaneously measuring a plurality of ionic activities at the surface of organic tissues or in a fluid. A shunt is assigned to each of these membranes and contacts them electrically. Each membrane is held in the carrier so as to be electrically insulated and secured against the penetration of moisture. One of the electrodes, each of which comprises a membrane and a shunt, is constructed as a reference electrode, or a reference electrode is provided as a separate structural component part with a respective contact at the organic tissue or fluid, while the remaining electrodes serve as measuring electrodes in that at least all the measuring electrodes are comprised in a sensor body and in that the carrier and the sensor body are held securely to one another.

Human and animal organs and tissues are coated in vivo by a thin liquid film of interstitial fluid. The ions contained in this liquid film are a good indication for the functioning of the respective organ and can be measured by the invention. In addition, conclusions can be drawn about the functioning of the smallest areas to the level of the capillaries (microcirculation), even over spatial distribution of the individual ionic activities. By using the invention, specimens need not be taken, nor is any damage done to the tissue to be measured. During dialysis, continuous measurements are possible directly in the blood of the patient without the stress caused by blood removal. Direct blood measurements enable an "on-line monitoring" without time delays.

In measurements of ions, a distinction is made between ion concentrations and ionic activities. Ion concentration is the totality of the individual ions (e.g., all sodium ions) measured in the body or in the blood. For ionic activity, only the free ions which are not bonded with other substances are measured and accordingly can actively participate in the metabolic functions of the organs. Only these active ions can be trapped by ionophori, so that a change of the aforementioned phase boundary potential occurs at the measuring electrode.

Therefore, the areas of application of the invention lie first and preferably in the area of medicine, such as transplantation centers, surgical and intensive medical care units and in general medical technology. In addition, use is possible in the aforementioned dialysis treatment and in medical-pharmaceutical and biological research.

Accordingly, present risks in medical treatments can be significantly reduced by means of rapidly and simultaneously gaining important information on the electrolytic condition of individual organs (e.g., heart, kidney, brain, etc.), in the surgical (e.g., transplantation surgery) and other indicated medical areas.

As explained above, the measurement of biologically relevant activities of the different ions is possible, but so are ion measurements in nonmedical areas.

In addition, the directly contacting, ion-selective multiple-surface sensor of the present invention with its sensor body, carrier and membranes and the shunts assigned at the membranes, can form a movable unit which is connected to a computer or the like (computer-controlled measurement data processing with standardized digital interfaces) via only one connecting cable. The sensor is movable relative to the computer and, therefore, can be placed, e.g., at every desired place on an organ for the purpose of carrying out the measurement. An organ is not only one of the organs mentioned above by way of example, such as the heart, kidney or brain, but also the skin of a patient. The sensor can be placed on the surface of the skin and the required measurements carried out. The aforementioned movability or portability of the measuring arrangement is of great advantage in the medical, biomedical or pharmaceutical areas of application for the use of this sensor in practice. Also included in the aforementioned portability, in particular, is that such a sensor, with the respective electronic device, is relatively small and movable, e.g., can be brought along in a helicopter or, for another example, can be transported without difficulty from an operating suite to another room.

Moreover, each membrane is electrically insulated so that there is protection against moisture penetration and all measuring electrodes are comprised at or in a common sensor body. The reference electrode which is provided in addition, is preferably one of the electrodes held in or at the sensor body, since this is the most economical and most favorable construction, and is also the smallest with respect to spatial requirements. However, in special cases or, if desired, a separate reference electrode can also be provided as indicated. With respect to the above, it is emphasized that the term "electrode" is understood to be the unit comprising a membrane and the shunt belonging to it. The carrier protects the membranes against mechanical damage.

For the sake of completeness, it is noted that a hollow cylindrical body is known from German DE-OS 29 27 948, in whose interior a piston is displaceable so as to slide in a tight manner. The front face of this piston is provided with metal electrodes or glass electrodes which project from the piston head and carry out measurements in a fluid which is to be introduced into the piston. Although glass electrodes are ion-selective, measurements can only be carried out with the latter in fluids and not on the organ surface as in the present invention.

Another substantial disadvantage of the arrangement according to DE-OS 29 27 048, and a similar arrangement according to German DE-OS 29 24 117, consists in that these electrodes require a multiple of the space or the contact surface taken up by a sensor and membrane arrangement according to the present invention. This difference can amount to more than a factor of ten. Finally, the German references just mentioned do not provide structures for measuring the activity of ions by means on plural ion-selective membranes and respective shunts and also do not show the characteristic features and advantages of the present invention as indicated above.

According to the invention, all membranes of a carrier can be adjusted to a determined ion. This provides the possibility of measuring the distribution of the activities of the same ion over a determined body surface and showing this numerically, i.e., digitally or graphically. On the other hand, it is also possible with the invention that each of the membranes of a carrier be adjusted to a different ion. By means of this, the activities of different ions can be determined with one and the same sensor simultaneously. Measurements of combinations of the two aforementioned possibilities are also conceivable according to the invention.

According to a preferred embodiment of the invention, the above-mentioned movability of the sensor can be effected by means of a holding device at which the sensor is attached. The holding device is either constructed as a handle or is provided with a handle. This substantially simplifies and broadens the use of the sensor in practice. It is particularly advantageous if the sensor can be exchanged easily with a sensor having other membranes. When there is a holding device, the respective sensor is to be fastened to it so as to be detachable, wherein there is a detachable contact connection between the shunts of the sensor and corresponding connections of the holding device. The membranes of the other respective sensors can be different from the preceding sensor, according to type and quantity. Accordingly, it is adaptable to various special requirements.

A computer electronic device can be provided and at least partially accommodated in the holding device. The same is true of an impedance converter which is functionally provided between the respective sensor and the computer electronic device. The part of the computer electronic device which is not accommodated in the handle can be portable. Such a measuring system (sensor measurement of ionic activities; sensor-holder-impedance converter and signal amplifier; analog-to-digital conversion to computer and measurement data processing) can not only be used in a stationary manner, but also can be used as a transportable measuring system (including the transporting possibility provided by the holding device) due to its movability or portability as explained.

In a preferred construction of the invention, the membranes are arranged close to one another spatially on the smallest possible surface area, e.g., in the form of a circle, a spiral, a line or a so-called matrix. This makes it possible to carry out measurements on a very small surface with a sensor that is compact and therefore easy to handle and which is placed on the organ surface with a large quantity of identical or different ion-selective membranes.

In order to be able to accommodate the provided quantity of shunts in a small space so as to be insulated, a sensor body can be provided according to a preferred embodiment of the invention, which sensor body comprises a series of layers which are securely connected to one another. These individual layers comprise conductive structures to form the shunts which are insulated from one another externally and form contact front faces at a front face of the sensor body. Each of these shunts is connected to a respective connection contact or a connection surface of the sensor body, preferably on its uppermost layer, so as to conduct electrically. A multilayer substrate is preferably provided for this purpose which comprises ceramic foils or polymer foils which are provided with the shunts and lie one above the other in a layered manner and are connected with one another.

The carrier of the membranes can be a separate part, according to the construction of the invention, which lies on a front face formed by the respective sensor body and is fastened to it. The contact surfaces or faces of the shunts are located in the front faces of the sensor body and contact the corresponding reciprocal or counter surfaces of the membranes (see the above constructions regarding the phase boundary potential).

As an alternative to the latter embodiment, the carrier and sensor body can also be constructed in one piece. For this purpose, the ends of wires which are insulated from one another and brought together to form a bundle, can serve as shunts. These bundles are held together by means of a casting, potting or pourable sealing compound which, at the same time, forms the sensor body and the carrier for the membranes. Such a sensor can be substantially elongated and constructed so as to have a very small diameter (smaller than in the previously explained embodiment). It is therefore suitable particularly as a probe for introduction into a human body, wherein it can remain in the body for several days in order to carry out measurements. Subsequently, this probe can be removed. The aforementioned measurements can be, for example, measurements on the surface of an organ.

In both of the aforementioned cases, a good electrical contact in the sense of the invention is made possible between the shunts and the respective membranes.

The use of such a sensor for hemodialysis has already been mentioned. For this purpose, according to another suggestion of the invention, a respective arrangement and at least two sensors can be provided, one of the sensors (the first) being connected in a circulation path through which the blood of the patient flows, at a place arranged downstream of the dialyzer in the direction of this circulation path, and the other sensor being connected in the flow of the dialysis fluid at a place located prior to the dialyzer in its flow direction for the purpose of ion-selective measurement of the blood and the dialysis fluid. The measurement results of the two sensors are fed to a control device for the purpose of controlling and regulating the composition of the dialysis fluid and a reference or desired value of the purified blood is made available to the control device. This advantageous ion-selective measurement which is preferably effected in a temperature-compensated manner is accordingly constructed as a hemodialysis measuring device for controlling the dialysis fluid mixing system, which hemodialysis measuring device measures two circulations, namely the blood circulation and the circulation of the dialysis fluid with respect to their content of determined chemical components, e.g., potassium. The respective contents of determined chemical components in the two circulations must be adjusted to one another so that the respective quantity of these chemical components in the dialyzer (so-called "artificial kidney") can pass from the blood circulation into the circulation of the dialysis fluid and, possibly, vice versa. The measuring data necessary for this and particularly for adjustment of the chemical components of the dialysis fluid are provided by the sensors according to the invention and fed to the respective control device. The arrangement according to the invention works "on line" specifically during the dialysis process. The blood used for measurement need not be rejected or lost for the purpose of measuring.

In a preferred embodiment of the invention, another (third) sensor is provided for the ion-selective measurement of the blood, which sensor is located prior to the dialyzer in the direction of circulation of the blood, its measuring data likewise being fed to the control device. This third sensor cooperates with the aforementioned first sensor such that "purification" of the blood is monitored accordingly and poor "purification" is detected. Under certain circumstances, "purification" which is too rapid can occur which stresses or even endangers the patient. Both of the aforementioned cases can be detected by means of the cooperation of this third sensor with the aforementioned first and second sensors and can be reported to the control device and/or to monitoring personnel.

Finally, according to another suggestion of the invention, another, fourth, sensor can be connected in the course of the dialysis fluid, which fourth sensor is located downstream of the dialyzer, and whose measurement data are likewise fed to the control device. The cooperation of this fourth sensor with the aforementioned second sensor makes possible corresponding reciprocal control, wherein the second sensor serves to monitor the dialysate mixing system and the fourth sensor serves to monitor the electrolyte loss quantitatively during dialysis.

In principle, dialysis devices comprise a dialyzer ("artificial kidney"), a blood monitor and a monitor controlling the dialysate composition. For this purpose, it is advantageous if the sensors with their sensor bodies being accommodated in each instance in a measuring cell, produce the respective connections without difficulty and in order to be able to detach them again when required. Such a measuring cell can be fastened at the aforementioned monitors. The aforementioned measuring cells have connection points.

According to another embodiment of the invention, an additional connection point for the connection and feed of calibrating fluid and a duct from this connection point to a three-way stop cock can be provided. Another duct leads from the three-way cock to the connection point for the fluid feed. The three-way cock is movable into two positions as desired. In the first position, it serves to connect the connection point for the calibrating fluid with the sensor and, in the other position, it serves for a connection of the connection point for the fluid feed with the sensor. This makes it possible to carry out calibration with such measuring cells, wherein a transition can be made from the measurement of the respective fluid to the calibration and vice versa by means of the three-way cock without interruption and without detaching the connections. Thus, intermediate calibrations are possible. It is only necessary to compose the calibrating fluid so that it can be added to blood or dialysate fluid. The "on-line" measurement already mentioned which can be effected in a continuous manner, can also be carried out continuously as a calibrating measurement. A transition can be made to the actual fluid measurement again without the loss of time. In this case, as well, special drawing of blood is unnecessary and blood losses do not occur.

A temperature sensing device, such as a thermometer probe which is built into the sensor, is particularly advantageous in dialysis in order to supply the necessary temperature correction to the control device or to the computer. An ion-selective, temperature-corrected, dialyzing device with dialysate mixing system is thus obtained for exactly adapting the electrolytes contained in the dialysate to the particular conditions or blood composition of the respective patients.

Another advantageous construction of the invention with respect to the membranes and their arrangement in the carrier consists in that two or more different membranes are provided one above the other in a carrier and in that each membrane contacts the adjacent membrane. The aforementioned membranes, arranged one above the other, form a "column". It is self-evident that a plurality of these "columns" are provided in a joint carrier according to the principle of the invention discussed in the beginning, wherein this carrier is put together with a sensor body, or this carrier and the sensor body can be a one-piece unit. In so doing, the fluid to be measured migrates from the outer contact surface through the individual membranes. With this arrangement, it is possible to bond or absorb interfering ions which are present in the substance or fluid to be measured through one of the membranes. This increases the accuracy of the measurement of the respective ion, wherein, however, no more surface area is needed than in the embodiments in which only one membrane is provided in each opening or recess of the carrier.

Another object of the invention consists in providing method steps for producing the sensor body with shunts and/or the carrier with membranes. Thus, for example, the above-described embodiment in which the carrier and the sensor body are constructed in one piece from casting compound, is produced in such a way that the wires of the bundle are first connected to one another and then cast with the casting compound and that the metal cores of the wires are then removed, e.g., etched away, from the front side of the casting compound forming the carrier corresponding to the thickness of the membranes, and that the membranes are then introduced into the recesses thus formed.

The various features of novelty which characterize the invention are pointed out with particularity in the claims annexed to and forming a part of this disclosure. For a better understanding of the invention, its operating advantages and specific objects attained by its use, reference should be had to the drawings and descriptive matter in which there are illustrated and described the preferred embodiments of the invention.

DESCRIPTION OF THE PREFERRED EMBODIMENTS

Figure 1:
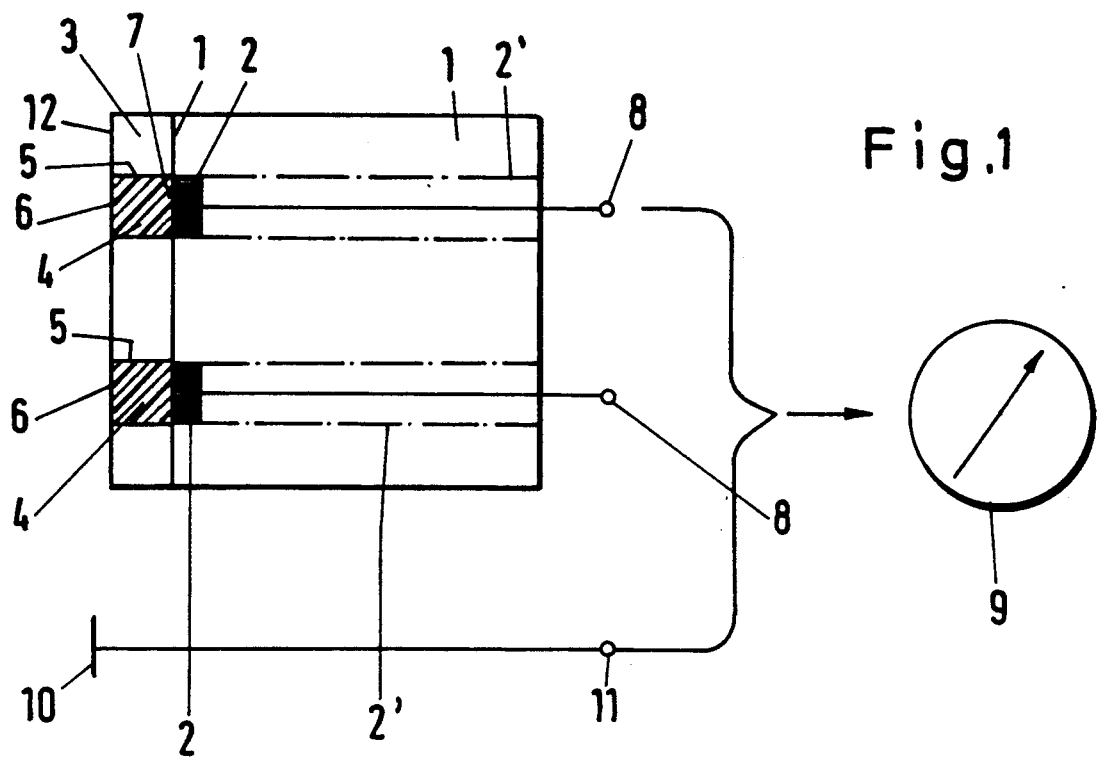
FIG. 1 is a longitudinal sectional and schematic view of a first embodiment of the invention.

FIG. 1 shows the principal construction of the invention with a sensor body 1 which receives and holds shunts 2, and a carrier 3 for receiving and holding the membranes 4. Each membrane with its respective shunt forms a unit defined as an electrode. The carrier 3 lies on the front face or surface 1' of the sensor body 1 and is securely held thereon. Two membranes 4 are provided in this example. By means of the material of the carrier 3 which is preferably a polymer, the membranes 4 are electrically insulated from one another and it is simultaneously ensured that no gaps occur at the side contact surfaces 5 between the membrane material on the one hand and the carrier material on the other hand, through which moisture could enter or even penetrate through. Accordingly, parasitic effects are prevented. Such gaps would lead to a short circuit between the outer contact surface 6 which is intended to be placed at a living body or organ surface or the like, and an inner contact surface 7 of the membrane which contacts the respective shunt. Also, it would no longer be possible to selectively measure the phase boundary potential for corresponding ions if gaps occurred at surface 5. The measurement results aimed for thus could not be achieved in cases where moisture entered or penetrated through a gap at 5, or they would at least be considerably falsified. The cross section of the membranes 4 could be configured differently, but it preferably would have the circular shape shown in FIGS. 2 and 5 which is advisable for achieving the explained tightness against moisture.

As indicated by reference numeral 2' in dash-dot lines, the shunts 2 which make electrical contact with the membranes 4, can be guided through the entire sensor body 1. The shunts 2 end in connections 8 which can be guided to an electronic computer device or to some other measuring or processing arrangement schematically symbolized at 9.

At least one of the aforementioned electrodes 4, 2, is a measuring electrode. The other electrode can have the function of a reference electrode. The reference electrode is connected at the organ surface or the fluid to be measured. This combination of the measuring electrode or measuring electrodes and the reference electrode at a sensor body 1 is the preferred embodiment of the invention. However, in special cases, it is also possible—and this variant is shown in FIG. 1—to provide a separate reference electrode 10 and to guide it to a separate connection 11, which is likewise connectable at the computer 9 or the like. This reference electrode 10 can comprise a corresponding membrane with shunt, just like the measuring electrodes 4, 2. However, it can also be constructed differently.

The respective reference electrode forms a constant reference point for the measuring electrode or measuring electrodes of the sensor for the purpose of measuring the voltage differences between it and the individual measuring electrodes. Thus, the shunts and membranes of the ion-selective sensor are one half of a measuring circuit, whose other half is formed by the reference electrode.

Each unit comprising membrane and shunt, that is, each electrode, is electrically insulated from the other electrodes. The electrodes are comprised in groups at or in the respective sensor body which is easily exchangeable at the respective holding device. This will be explained in more detail in the following.

The outer surfaces 6 of the membranes 4 are flush with the outer surface 12 of the carrier for the purpose of contact with the organ surface or the fluid.

Figure 2:
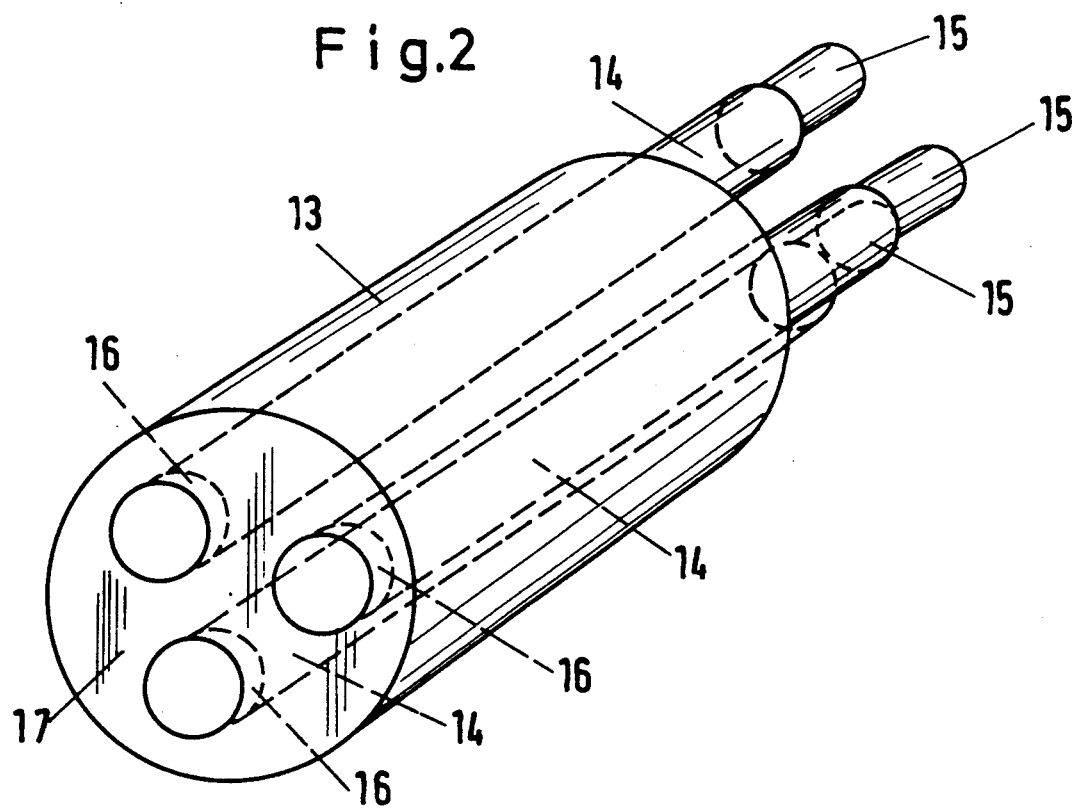
FIG. 2 is a perspective view of another embodiment of the invention.

FIG. 2 shows another embodiment of the invention in which the sensor body 1 and the carrier 3 are combined as a part 13, making up a unit in itself, comprising a casting compound, e.g., a polymer. The shunts 14 which are constructed as wires with insulated connections 15 are located in the casting compound as are the membranes 16 which are embedded in the front face 17 of the casting compound. Front face 17 is shown at the left in FIG. 2. The shunts 14 are first produced with casting compound 13 in a continuous casting, e.g., by means of bundling the shunts 14 and casting around them with the casting compound. Recesses in which the membranes 16 are accommodated can then be provided on the front face 17 by means of etching away the shunts.

The following explanations of FIGS. 3 to 6 will be referred to with respect to the details of the fastening and moisture-tight arrangement of the membranes within the carrier (this also applies to FIG. 1).

It can be seen that instantaneous ionic activity can be measured at the surface of the organ of a body, i.e., noninvasively, with the possibility of drawing conclusions about the microcirculation in tissues and organs accordingly. A large quantity of identical ions can be measured simultaneously by the sensor with the presence of identical membranes and, in another construction with different membranes, different ions, e.g., $H^+$, $K^+$, $Na^+$, $CA^{2+}$, etc. can be measured simultaneously with the sensor in each instance in a very small space. The distribution of the ionic activities along the surface can be measured and shown to simultaneously correspond to the respective spatial arrangement of the membranes. The aforementioned measuring possibilities can also be provided at a sensor so as to be combined.

The embodiment of FIGS. 3 to 6 shows the composition of a sensor or sensor body having a plurality of layers which are laminated with one another to form a so-called multilayer substrate. Lamination is understood here as a technique which brings together such layers under pressure and temperature and "bakes" them onto one another so that they are intimately connected with one another. In each instance, the four layers designated 18 to 21 can be a ceramic foil or a polymer foil, for example. The foils are then fired or cured in an oven. This technique is known. Of the four insulating substrate layers 18 to 21 shown here, the three lower substrate layers 19 to 21 are provided with conductive lines or structures 22 which can comprise inert precious metals, e.g., gold or platinum, and form the shunts, wherein their front faces 23 which lie on the right-hand side in FIG. 3, correspond to the faces 7 in FIG. 1. These front faces 23 are flush with the respective front faces 24 of the layers 18 to 21. The structures 22 which are brought together in the area of the front face 23, 24 for the purpose of accommodating the membrane on a surface which is as small as possible, are guided apart at the opposite end of the layers 19 to 21, which end is on the left-hand side in FIG. 3. Structures 22 are connected to connection surfaces 26 of the uppermost layer 18 shown here by means of contacts 25 so as to be electrically conductive. The connection surfaces 26 correspond to the connections 8 of FIG. 1 and are likewise connected to a computer, electronic device or the like. This connection is preferably constructed in the form of a plug-in connection so that different sensors can be connected to the computer, electronic device or the like, in a rapid and simple manner (see FIG. 9).

Figure 3:
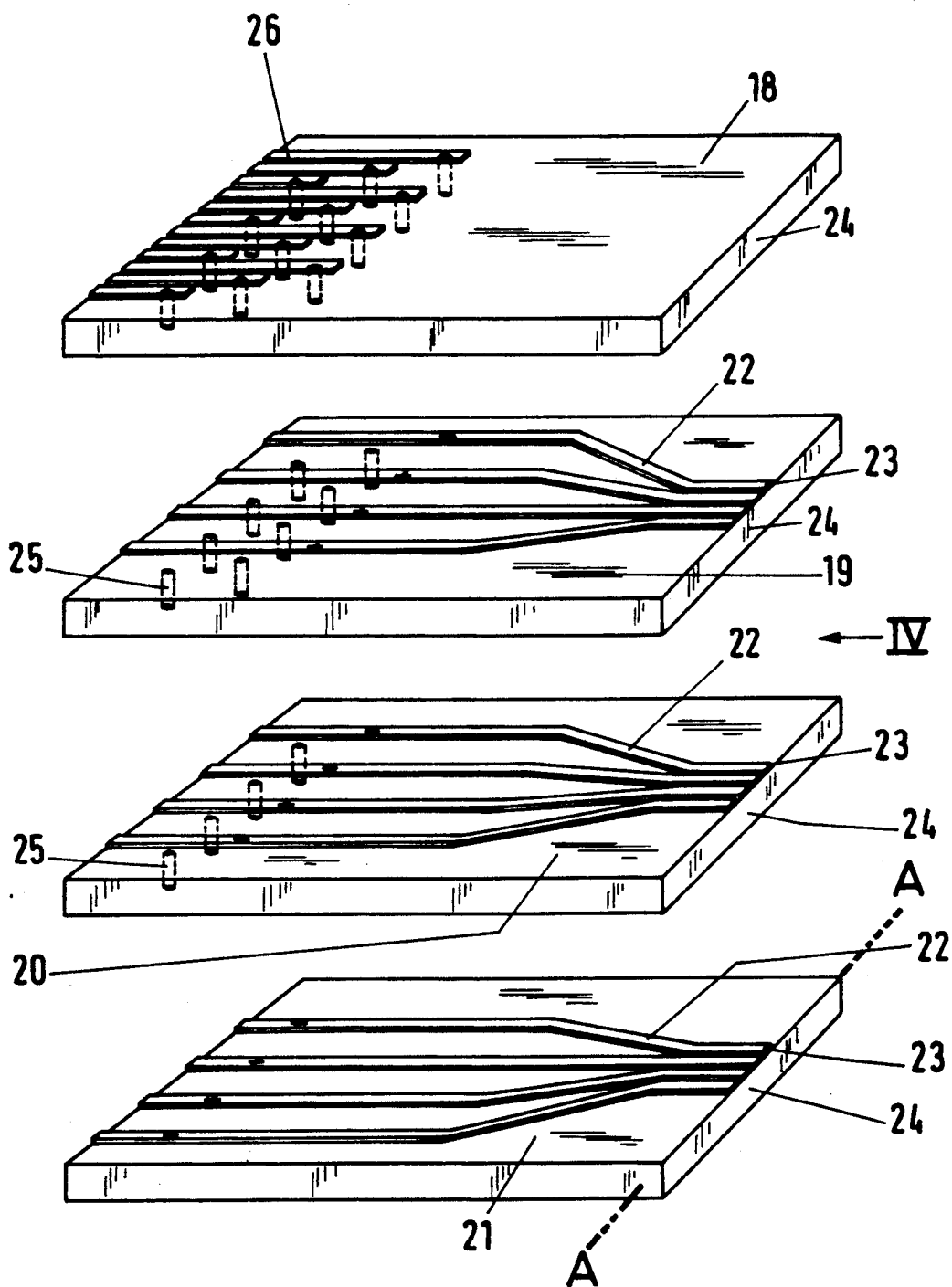
FIG. 3 is an exploded view showing the individual layers of a multilayer substrate according to the invention, but without carrier or membranes.
Figure 6:
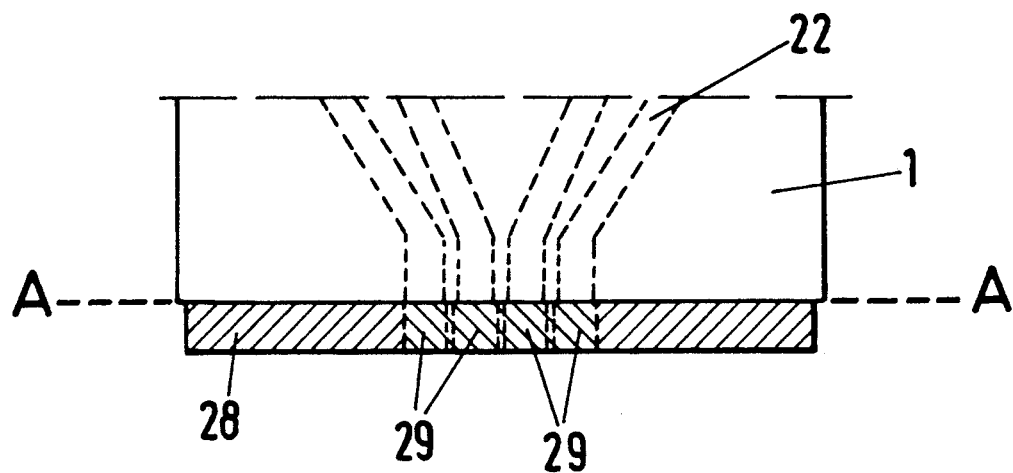
FIG. 6 is a top view taken in the direction of arrow VI in FIG. 5, partly in section.

After lamination and firing or curing of the sensor body, the side shown at the right in FIG. 3 is mechanically processed (e.g., by sawing or grinding) along the section line A—A in FIG. 6 in such a way that the conductive structures 22 contact the surface with their front faces 23 and electrical contact is made with the membranes 29 to be described in the following.

The carrier 28, e.g., a polymer layer, is cast on the front face 24 of the multilayer substrate or securely applied in some other manner. The membranes 29, indicated in FIG. 6 by means of opposite hatching, are either already contained in the carrier 28 prior to its fastening at the multilayer substrate or they are introduced into it after its fastening at the multilayer substrate. In addition, openings can be produced in the carrier by means of electrical discharges, laser beams or the like, the membranes being inserted into these openings. It is particularly recommended to introduce the membranes in the form of solutions, wherein the membranes comprise the desired characteristics after evaporating the solvent. A particularly intimate connection, and one which accordingly blocks moisture from penetrating, is achieved between the membrane material and the carrier material by means of this. However, the membranes can also be worked out of a foil-like material in their basic form by mechanical means (e.g., by means of punching) and can be fastened in the openings of the carrier by means of a cementing material or solvent and cemented so as to be tight against moisture. The membranes 29 contact the front faces 23 of the shunts 22 directly so as to be conductive in this embodiment as well.

Figure 4:
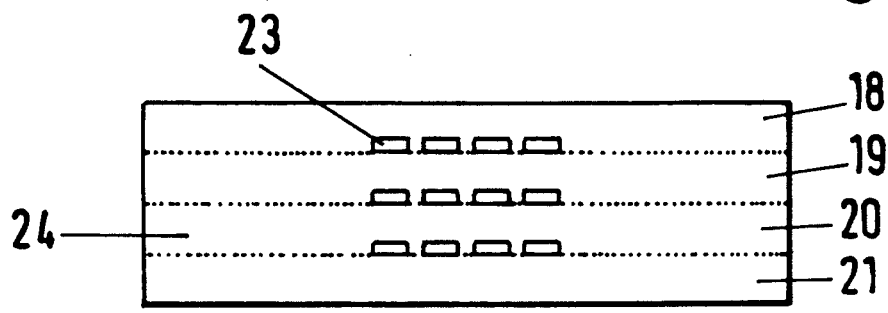
FIG. 4 is a front elevational view in the direction of arrow IV of a sensor body according to FIG. 3.
Figure 5:
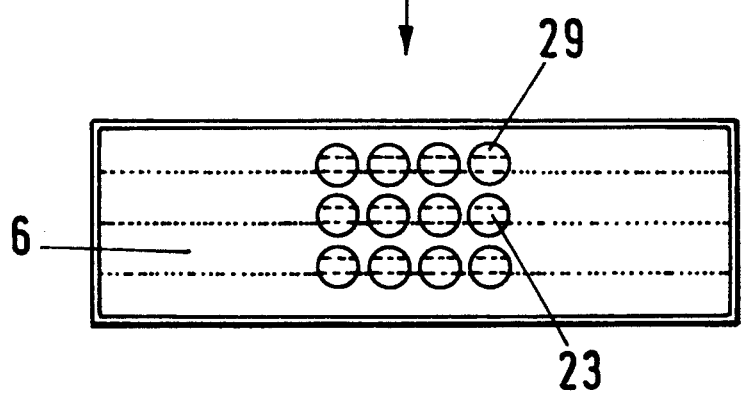
FIG. 5 is a view analogous to FIG. 4, but with the membranes and their carrier included.

FIGS. 4 and 5 show a, e.g. matrix-like, structure of the front faces 23 or membranes 29. This means that a correspondingly large quantity of conductive contact points (membranes) can be accommodated on a very small surface (e.g., 4 membranes on a surface of $1 \times 1$ mm$^2$). Instead of this matrix-like arrangement, for example, in three rows to every four membranes, the membranes could also be arranged differently, e.g., in a plurality of concentric circles, in a spiral shape, or the like. On the other hand, the respective connection surfaces 26 can be accommodated at the layer 18 on a substantially larger surface relative to the surface occupied by the membranes. This is particularly advantageous in the case of a detachable plug-in connection.

Figure 7:
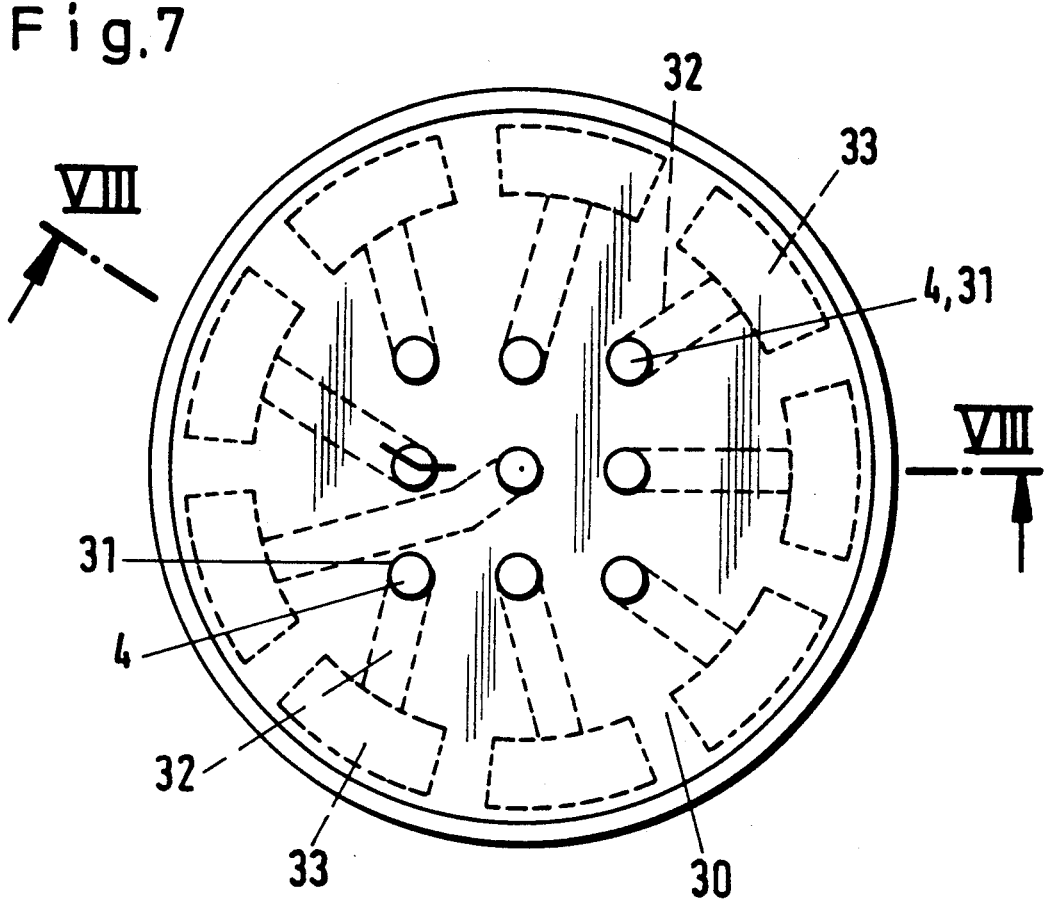
FIG. 7 is a top plan view of another embodiment of the invention.
Figure 8:
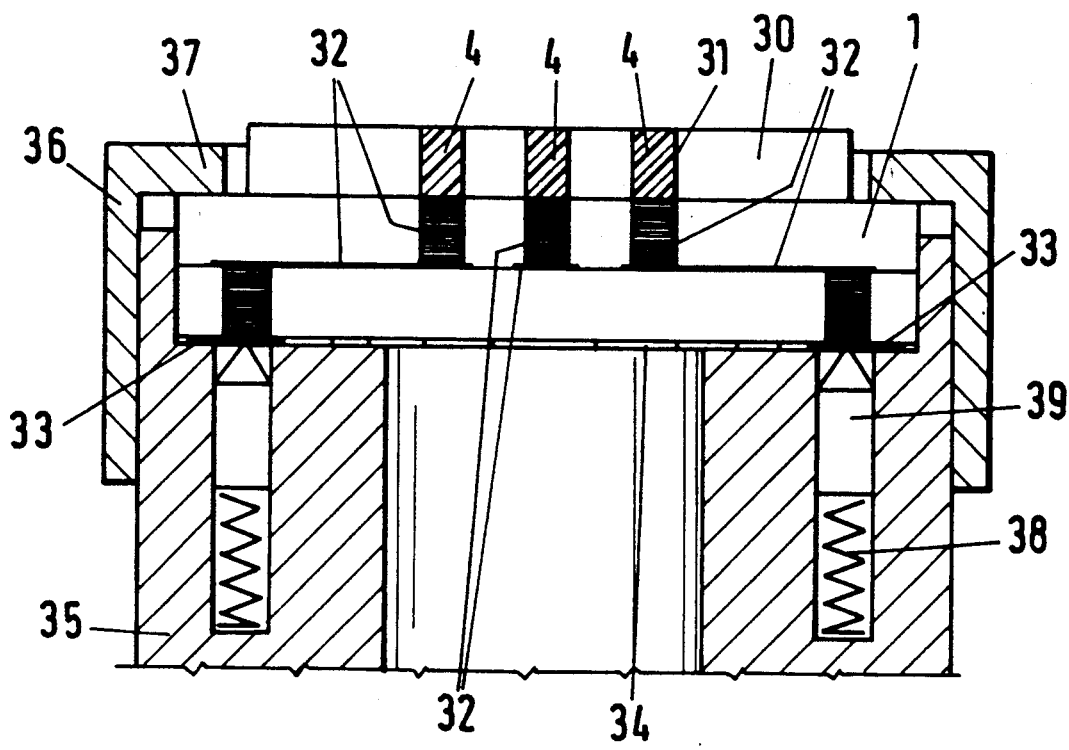
FIG. 8 is a sectional view taken on line VIII—VIII in FIG. 7.

In the embodiment of FIGS. 7 and 8, a carrier 30 in the form of a cylindrical circular disk, is provided with membranes 4, as in the construction according to FIG. 1. The membranes are embedded in openings 31 so as to be tight against moisture. Each membrane is connected at its underside to a contact point 33 via s shunt 32, which contact point 33 is located at the outer circumference of the lower surface 34 of a sensor body 1 shown in FIG. 8. With this outer circumference comprising the contact points 33, the sensor body 1 rests on the upper surface of a cylindrical holder 35 (FIG. 8). This holder is secured by means of a retaining nut 36 which grasps the upper area of the sensor body 1 in FIG. 8 and the outer area of the sensor body 1 with its inwardly facing edge 37 and presses it against the holder 35. Contact pins 39 which contact the contact points or surfaces 33 are biased and supported by springs 38 in the holder 35. The sensor body 1 can be laminated (see the preceding embodiment). This embodiment of the invention is producible at relatively low cost. The retaining nut 36, 37 provides a very good seal. In the embodiment of FIGS. 7 and 8, carrier 30 which consists of a polymer, for example, is securely connected to the sensor body 1 which comprises an aluminum oxide ceramic foil for example. However, the carrier and sensor body 1 can also be produced from the same aluminum oxide ceramic foil and can be fused with one another by means of heating so as to form a unit (not shown).

In principle, it is true that the sensor can consist of sterilizable material in case of use for medical purpose.

Figure 9:
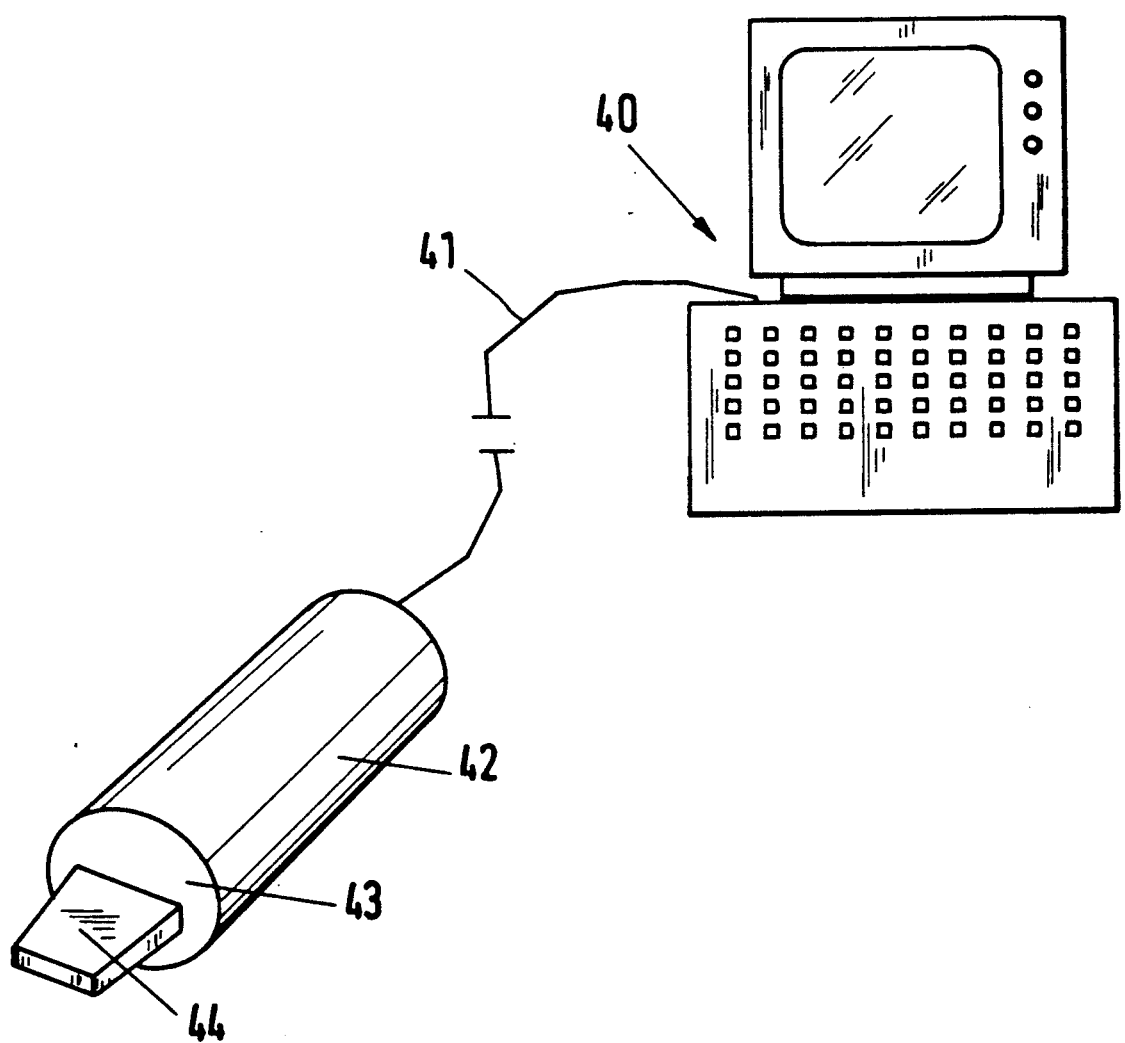
FIG. 9 is a perspective view of a movable, portable arrangement according to the invention.

FIG. 9 shows an illustrative view of the computer electronic device 40 with a flexible, movable feedline 41 to a holding device 42 which can be constructed itself, with respect to its shape, as a handle, or with a handle. The sensor which has the reference numeral 44 in this case is detachably placed on the outer end 43 of the holding device 42. This easy and rapid exchanging possibility of the sensors is of substantial importance particularly during operations. This can be effected, e.g., in the embodiment of FIG. 3, in such a way that the connections 26 are guided out to the left in this drawing and end in plugs which fit in plug-in openings of the end 43. Also, the holder 35, according to FIGS. 7 and 8, can be constructed at its end with corresponding plugs which are connected to the contact pins 39.

In addition, a temperature sensing device can be integrated in the sensor or a temperature measuring device can be provided. The measured temperature is then input to the computer 9 or 40, or the like, for automatic temperature correction.

A so-called impedance converter can be provided between the outgoing contacts 8, 11, 15, 26, 33 on the one hand and the computer electronic device 9, or the like, on the other hand. This has the object of converting very high-resistance (high-impedance) signals occurring because of the measurement principle of the ion-selective measurement into low-resistance signals which can then be transmitted via a line. This high resistivity causes a corresponding susceptibility to interference in measurements. Therefore, in order to achieve a sufficient screening from environmental influences, the aforementioned impedance converter is to be provided, if possible, directly at the sensor. Only in this way is a cable length of up to 5 m achievable, which is necessary, e.g., for operations. A converter for converting the analog low-resistance signals transmitted by the impedance converter into digital signals for the computer can then be connected to this impedance converter.

The impedance converter, the analog-to-digital converter and at least a part of the computer electronic device are advantageously provided in the handle 42. This results in the advantage of very short line routes or direct link connections from the sensor to the impedance converter and from the latter to the analog-digital converter, as well as from the latter to the computer electronic device.

Figure 10:
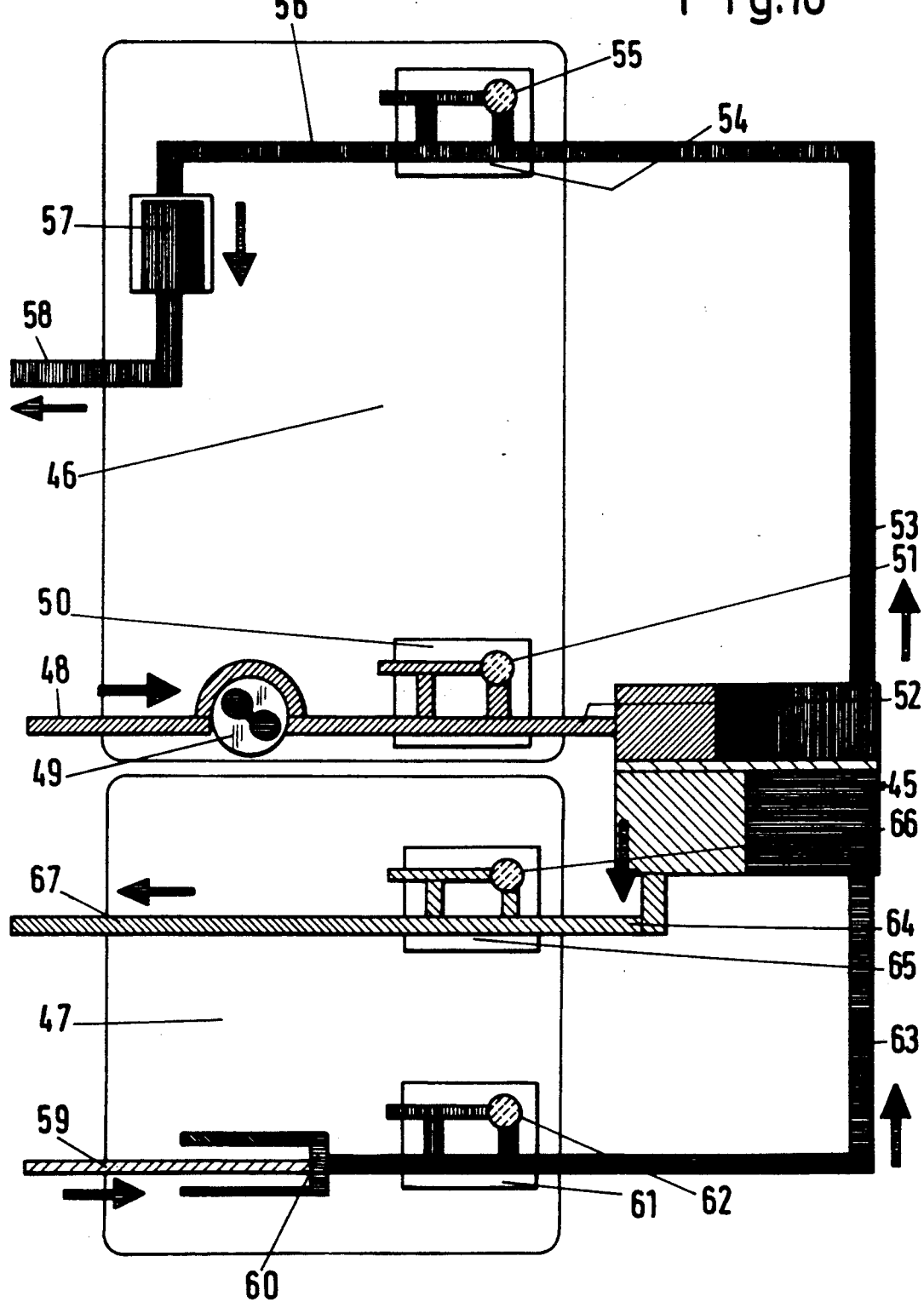
FIG. 10 is a schematic diagram of a dialysis arrangement with respective sensors according to the invention.

FIG. 10 shows a dialysis arrangement comprising a dialyzer (so-called "artificial kidney") 45, a blood monitor 46 and the dialysate monitor 47 as well as the lines, sensors and other structural component parts which are explained in more detail in the following.

Figure 14:
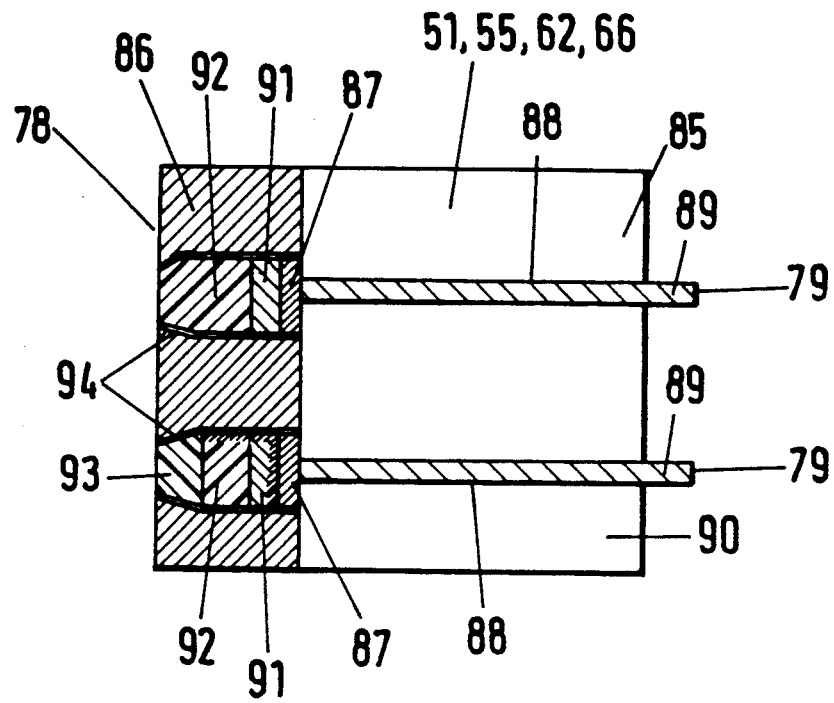
FIG. 14 is a schematic and sectional view of the construction of a sensor, according to the invention, with a plurality of membranes located one above the other.
Figure 15:
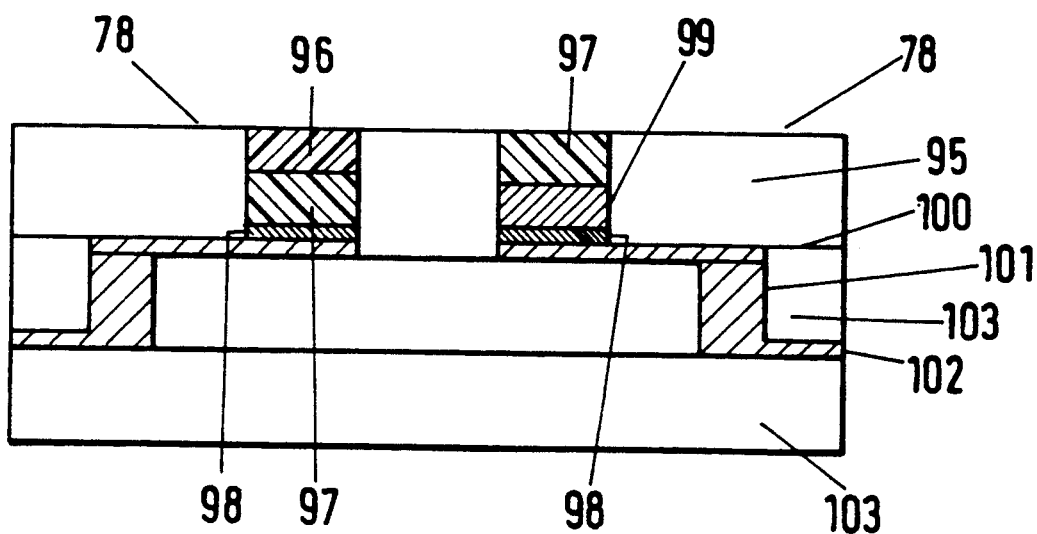
FIG. 15 is a sectional view of another variant of the construction of the sensors, according to the invention, with a plurality of membranes arranged one above the other.

As regards the construction and design of the sensors, the preceding constructions, and the embodiments according to FIGS. 14 and 15 are referred to. The blood is fed through the line 48 from the patient by means of a blood pump 49 to a third measuring cell 50 with a third sensor 51 and from there via a line 52 to the dialyzer 45. After the so-called blood wash, the purified blood is fed via line 53 to a first measuring cell 54 and, accordingly, to a first sensor 55. From there, the blood reaches an output line 58 via a line 56 and an airtrap 57 and arrives back in the body of the patient again. The dialysate fluid is fed through the line 59 and via a dialysate mixing system 60 to a second measuring cell 61 with a second sensor 62, and from there to the dialyzer 45 via a line 63. The dialysate fluid flowing out of the dialyzer reaches a fourth measuring cell 65 with a fourth sensor 66 through the line 64 and then arrives at the outflow line 67.

As already explained, the so-called purification of the blood is monitored between the first sensor 55 and the third sensor 51, while the second sensor 62 serves to monitor the dialysate mixing system, and the fourth sensor 66 for quantitative monitoring of the electrolyte loss during dialysis. At least the first sensor 55 and the second sensor 62 are required in order to monitor or control the dialysate mixing system by means of the first sensor 55 on the basis of the composition of the blood leaving the dialyzer 45, wherein the composition of the blood after leaving the dialyzer, i.e., at the sensor 55, forms the control variable for the adjustment of the dialysate mixing system. A computer 68, shown in a purely schematic manner in FIG. 12, can be provided that is connected via lines (not shown) to the outputs of the aforementioned sensors, whose measurement results it evaluates, and correspondingly controls the dialysate mixing system. For this purpose, a desired value of the composition of the blood can be adjusted in the computer 68.

Figure 11:
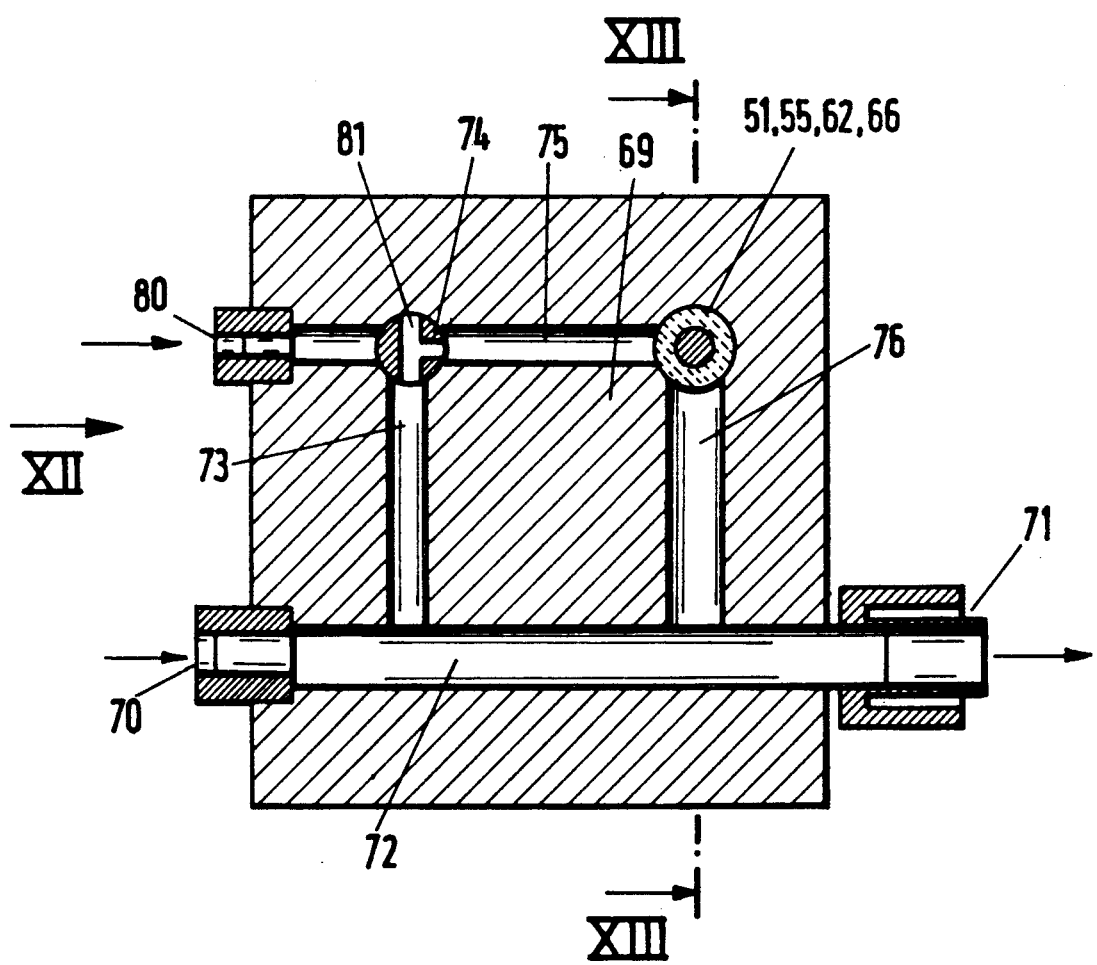
FIG. 11 is a sectional view taken through a measuring cell according to the invention and on line XI—XI in FIG. 12.
Figure 12:
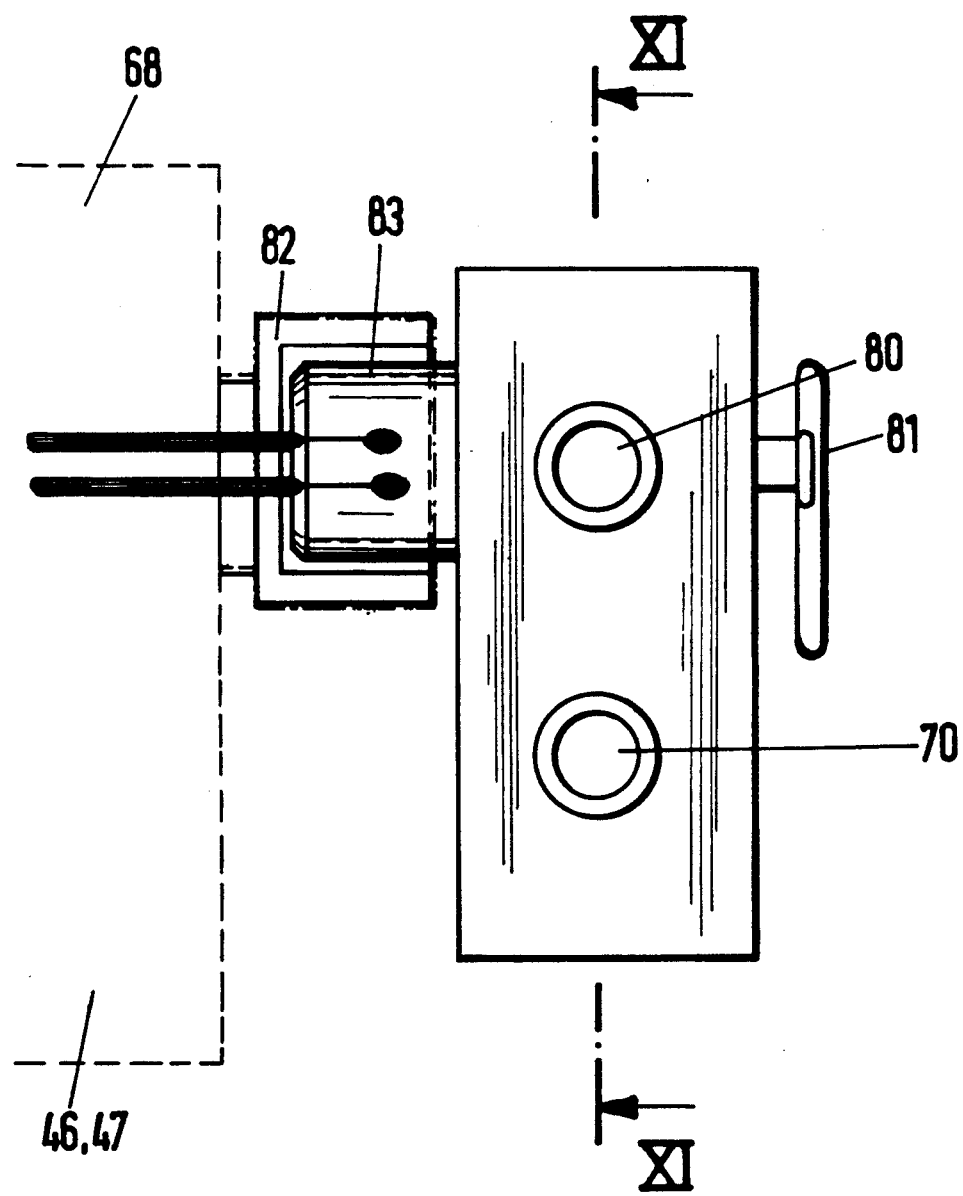
FIG. 12 is a view taken on line XII in FIG. 11.
Figure 13:
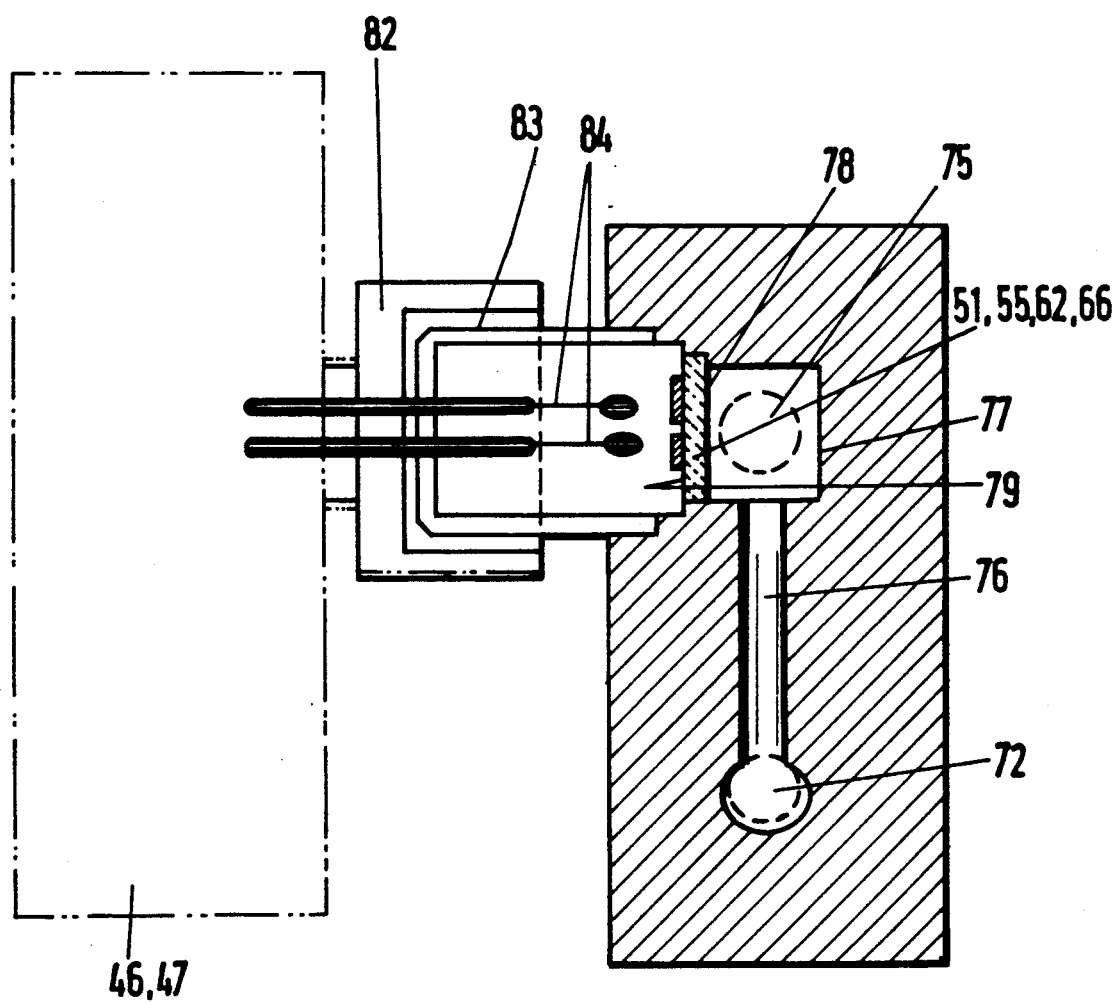
FIG. 13 is a sectional view taken on line XIII—XIII in FIG. 11.

The construction of the aforementioned measuring cells can be seen from FIGS. 11 to 13. The respective sensor 51, 55, 62 and 66 is accommodated and fastened within a measuring cell body 69. The fluid to be measured is fed at connection 70 and conducted away at connection 71. In a shunt across the connecting duct 72 between the two connections 70 and 71, the fluid to be measured is guided past the sensor via a duct 73 and a three-way stop cock 74 and another duct 75 (also see FIG. 13). The fluid is measured at the sensor and fed to the connection 71 via the duct 76. For this purpose, a measuring chamber 77 (FIG. 13) is provided adjacent the sensor, the ducts 75, 76 opening into this measuring chamber 77. The contact or measuring side of the sensor is numbered 78 and its connection side is numbered 79.

If the three-way cock is rotated in the counterclockwise direction by 90° out of the position shown in FIG. 11, the inflow of the fluid to be measured (blood or dialysis fluid) is stopped from entering the duct 73 and the inflow of a calibrating fluid is made possible from the connection 80 via a duct 81 to the duct 75 and, accordingly, to the sensor. The calibrating fluid, to the extent that it reaches the blood, is compatible with the blood and is sterile and an isotonic solution. Naturally, the entire measuring cell with sensor must be kept sterile.

The measuring cells are fastened at the blood monitor 46 and dialysis monitor 47, wherein these fastenings are preferably detachable. Retaining nuts 82 can be used for this purpose, each of which is screwed to an internal thread via an external thread of connecting pieces 83 which are located at the respective measuring cell. Accordingly, spring contacts 84 of the respective monitor are simultaneously brought into electrical contact with the connection side 79 of the respective sensor. The spring contacts produce contact connections between the sensors and the respective computer or control parts of the monitors or the computer 68.

FIG. 14 shows one of the sensors 51, 55, 62, 66 with sensor body 85, carrier 86 for the membrane to be explained in the following, shunts 87 and their connections 88 to connections 89. A plurality of membrane groups can be provided. One of the membrane groups together with the respective shunt, serves in the present embodiment as a reference electrode, and the other membrane group or membrane groups together with their respective shunts, serve as a measuring electrode or measuring electrodes. The contact or measuring side is also numbered 78 and the connection side is numbered 79. The carrier 86 comprises an insulating work material, e.g., a polymer. The sensor body 90 is constructed in such a way and from such work material that no electrical contact can be produced between the shunts 87 or their connections 88. The above constructions are referred to in particular.

A plurality of membranes are provided here in this embodiment at the bottom. Three membranes 91, 92 and 93 are provided one above the other as a group, wherein the membrane 91, shown in the cutout portion 94 in FIG. 14 at the farthest right-hand side, contacts the respective shunt 87 and, on the other hand, also contacts the membrane 92 located to its left which, in turn, contacts the additional membrane 93 which forms the outer contact surface of this membrane arrangement. In FIG. 14 at the top, only the two membranes 91 and 92 are provided. The individual membranes of such a column-like membrane arrangement are adjusted to one another. One of the membranes is the actual membrane for measurement and the other, or the two other membranes of the group, serves to remove or absorb interfering ions.

In order to produce such a membrane arrangement, one may proceed in such a way that the individual membranes are liquified within the cutout portion 94, at least in their edge areas, by means of dissolving with a solvent or by means of a melting process, wherein this membrane is securely and undetachably connected with the cutout portion after evaporation of the respective solvent or cooling. The cutout portion 94 can be reduced in diameter in a slightly conical manner (this conicity is sharply exaggerated in the drawing) in the direction of the membrane 92 or 93 which is located on the outside and forms the outer contact surface in order, accordingly, to achieve a particularly secure hold of the individual membranes within the cutout portion. The membranes can be produced from a foil, e.g., as ion-selective PVC membranes or also as electrolytic gel. Since the individual membranes or gels lie one on top of the other in any case, the moist or liquid substance to be measured diffuses through the individual membranes until the shunt.

While the construction, according to FIG. 14 described above, corresponds to the sensor construction according to FIG. 1, in principle, FIG. 15 which is discussed in the following, shows a sensor construction approximating FIG. 8. Two different membrane groups are provided in the carrier 95. In the membrane group on the left, a chemical membrane 96 for eliminating interfering ions is provided so as to be flush with the contact or measuring side 78. An ion-selective PVC membrane 97 is located below this and an Ag-AgCl layer 98 is provided below the latter in order to make contact. The construction of the membrane group on the right provides the ion-selective PVC membrane 97 so as to be flush with the contact or measuring side 78 as well as a KCl gel 99 located below the latter. The Ag-AgCl layer 98 in turn is located below the latter.

The individual layers or membranes 96 to 99 are in direct contact with one another in this embodiment also. The electrical signals occurring are directed via conductor paths made, e.g., as printed conductors 100, and through-connections 101 to additional conductor paths or contact points 102. These conductor paths can consist of silver (Ag). The sensor body is numbered 103. The carrier 95 can be a polymer for example. It is securely connected with the sensor body 103 which, according to this embodiment, can comprise aluminum oxide ceramic foils which are likewise securely connected with one another. But, instead of this, both the carrier 95 and the sensor body 103 could be produced from a corresponding quantity of aluminum oxide ceramic foils and baked with one another, wherein the foils fuse one inside the other and accordingly form a unit (not shown).

Accordingly, not only in the latter construction, but also in the corresponding variants of the embodiment of FIGS. 7 and 8, a unit of a carrier and sensor body, which unit is one piece in itself, is provided from the same material.

All of the characteristic features shown and described as well as their combination, are substantial to the invention. In particular, the characteristic features explained and shown possibly in connection with one of the embodiments, can also be used in a corresponding sense in another of the other embodiments.

While specific embodiments of the invention have been shown and described in detail to illustrate the application of the inventive principles, it will be understood that the invention may be embodied otherwise without departing from such principles.

What is claimed is:

1. A sensor for measuring the activity of ions at the surface of organic tissues or fluids, comprising an electrical insulating carrier, a plurality of ion-selective membranes supported in the insulating carrier and secured to the insulating carrier hermetically against the penetration of moisture between said membranes and said carrier, an electrical shunt connected to each membrane and forming with each membrane an electrode, a reference electrode operatively connected to said carrier for acting with at least one measuring electrode formed by at least one of said plurality of membranes and connected shunts, and a sensor body connected to said carrier holding at least all of said measuring electrodes to simultaneously measure a plurality of ionic activities with said plurality of membranes.

2. A sensor according to claim 1, wherein said reference electrode is formed by one of said ion-selective membranes with its connected shunt.

3. A sensor according to claim 1, wherein each membrane has an outer contact surface, an inner contact surface and a side contact surface connected between said inner and outer contact surfaces, said side contact surface being closely connected against said carrier for precluding the entry of moisture between said carrier and said membrane, said carrier having an outer surface coplanar with said outer contact surfaces of said membranes, said shunts of said membranes being engaged against said inner contact surfaces of said membranes.

4. A sensor according to claim 3, wherein said outer contact surfaces of said membranes are distributed on said outer surface of said carrier to form one of a circle, a spiral, a line and a matrix, in a closely spaced pattern on said outer surface of said carrier.

5. A sensor according to claim 1, wherein each of said membranes is made of different chemical substances adjusted to a selected ion so as to measure activity of the selected ion.

6. A sensor according to claim 1, wherein each of said membranes is made of different chemical substances adjusted to a different ion so as to sense the different ion.

7. A sensor according to claim 1, wherein said sensor with said carrier, said membranes and shunts, said reference electrode and said body are connected so as to form a portable single unit.

8. A sensor according to claim 7, including a holding device connected to said body for carrying said body, said carrier and said membranes and shunts.

9. A sensor according to claim 8, including computer means for computing ion activity, connected to said holding device, said holding device including connector means for interconnecting said electrodes to said computer means.

10. A sensor according to claim 1, including computer means for computing ion activity, and an impedance converter connected between said shunts and said computer means for transferring signals for measuring ion activity from said electrodes to said computer means.

11. A sensor according to claim 10, including a holding device connected to said body for carrying said body, said carrier and said electrodes, said impedance converter extending through said holding device for connection to said computer means.

12. A sensor according to claim 11, wherein said body with said carrier and said electrodes is detachably connected to said holding device so as to be replaceable by a different body having electrodes made of different selective membranes.

13. A sensor according to claim 1, wherein said carrier comprises polymer.

14. A sensor according to claim 1, wherein said body comprises a plurality of layers securely connected to each other, a plurality of conductive structures on each layer forming said shunts, each shunt extending to a common contact surface of said body, each of said membranes being connected to one of said shunts at said common contact surface, an uppermost one of said layers carrying connecting surfaces each connected to one of said conductive structures for establishing connection with each electrode.

15. A sensor according to claim 14, wherein said carrier is formed as a layer over said common contact surface in which said membranes are embedded.

16. A sensor according to claim 14, wherein each of said layers is made of one of ceramic foils and polymer foils.

17. A sensor according to claim 14, including through-connectors extending through at least some of said layers connecting some of said conductive structures to their respective connecting surfaces.

18. A sensor according to claim 17, wherein said connecting surfaces form a plug-in connection, and further comprising a holding device having a receptacle shaped so that said plug-in connection is receivable in said receptacle.

19. A sensor according to claim 1, wherein said body is in the form of a cylindrical disk, a holder for receiving said cylindrical disk and a retaining means engaged with said holder for fixing said cylindrical disk on said holder.

20. A sensor according to claim 19, wherein said holder has a contact surface, said shunts having contact points ending at said contact surface of said holder, and reciprocal contacts movably mounted in said holder engaging each of said contact points of said shunts.

21. A sensor according to claim 1, wherein said body and said carrier have facing engaged surfaces, said shunts each having a contact surface lying in said engaged surface of said body, each of said membranes having a contact surface lying in said engaged surface of said carrier whereby said membranes are in contact with said shunts, each membrane having an outer surface opposite from its contact surface for exposure to tissue or fluid.

22. A sensor according to claim 1, wherein said sensor is made of material that is sterilizable.

23. A sensor according to claim 1, including a temperature sensing device integrally formed in said carrier and adapted for connection to computing means.

24. A sensor according to claim 1, wherein said shunts each comprise a wire extending through said body, said body and carrier being formed as a single piece from a casting compound cast around said wires, said wires being spaced from each other in said casting compound.

25. A sensor according to claim 1, wherein at least one of said membranes comprises a plurality of adjacent contacting membrane layers.

26. A sensor according to claim 25, wherein at least one of said membrane layers is made of foil.

27. A sensor according to claim 25, wherein at least one of said membrane layers is made of PVC foil.

28. A sensor according to claim 25, wherein at least one of said membrane layers is made of gel.

29. A sensor according to claim 25, including a cutout portion in said carrier having a slightly conical shape, said plurality of membrane layers being disposed in said cutout.

30. A sensor according to claim 29, wherein one of said shunts extends to said cutout for contact with one of said membrane layers in said cutout.

31. A sensor according to claim 1, wherein the membranes are combined so as to form a single carrier.

32. A sensor according to claim 1, wherein the insulating carrier with the membranes is arranged at a first end face of the sensor body, the membranes in the insulating carrier being protected against passage of moisture, the shunts being carried from the membranes through the sensor body to junctions at a second end face located opposite to the first end face or a side surface of the sensor body, the membranes being arranged spatially close to each other on the first end face so as to permit simultaneous measurement of several ion-activities on an organic tissue surface.

33. A sensor according to claim 32, wherein the membranes are arranged on as small a surface as possible of the first end face.

34. A sensor according to claim 33, wherein the membranes are arranged to have a shape of one of a circle, a spiral, a line, and a matrix.

* * * * *

UNITED STATES PATENT AND TRADEMARK OFFICE
CERTIFICATE OF CORRECTION

PATENT NO. : 5,018,527

DATED : May 28, 1991

INVENTOR(S) : Werner Pfab et al

It is certified that error appears in the above-identified patent and that said Letters Patent is hereby corrected as shown below:

On the title page, item [73] the Assignee should read as follows:

--[73] Assignee: Siegert Gmbh
Fed. Rep. of Germany --.

Signed and Sealed this

Twenty-third Day of March, 1993

Attest:

STEPHEN G. KUNIN

*Attesting Officer*      *Acting Commissioner of Patents and Trademarks*